United States Patent [19]

Giannini et al.

[11] Patent Number: 4,925,674
[45] Date of Patent: May 15, 1990

[54] AMOXICILLIN MICROENCAPSULATED GRANULES

[75] Inventors: Robert P. Giannini, Plantation; Daniel A. Bashour, Boynton Beach, both of Fla.

[73] Assignee: hiMedics, Inc., Hollywood, Fla.

[21] Appl. No.: 236,375

[22] Filed: Aug. 25, 1988

[51] Int. Cl.$^5$ .............................................. A61K 9/26
[52] U.S. Cl. .................................. 424/469; 424/470; 424/494; 424/497
[58] Field of Search ............... 424/490, 489, 469, 470, 424/494, 497

[56] References Cited

U.S. PATENT DOCUMENTS

| | | | |
|---|---|---|---|
| 2,738,303 | 3/1956 | Blythe | 424/458 |
| 3,951,953 | 4/1976 | Khan | 424/19 |
| 3,966,899 | 6/1976 | Nakai | 424/468 |
| 4,083,949 | 4/1978 | Benedict | 424/19 |
| 4,138,475 | 2/1979 | McAinsh et al. | 424/19 |
| 4,177,254 | 12/1979 | Khan et al. | 424/19 |
| 4,193,985 | 3/1980 | Bechgaard et al. | 424/19 |
| 4,261,970 | 4/1981 | Ogawa et al. | 424/19 |
| 4,263,273 | 4/1981 | Appelgren et al. | 424/21 |
| 4,341,759 | 7/1982 | Bogentoft et al. | 424/21 |
| 4,349,531 | 9/1982 | Mlodozeniec et al. | 424/452 |
| 4,508,702 | 4/1985 | Hsiao | 424/22 |
| 4,518,019 | 4/1985 | Brancq et al. | 424/35 |
| 4,525,339 | 6/1985 | Behl et al. | 424/19 |
| 4,587,118 | 5/1986 | Hsiao | 424/19 |
| 4,606,909 | 8/1986 | Bechgaard et al. | 424/469 |
| 4,758,437 | 7/1988 | Sonobe et al. | 424/19 |

FOREIGN PATENT DOCUMENTS

| | | |
|---|---|---|
| 0012495 | 6/1980 | European Pat. Off. . |
| 2331375 | 6/1977 | France . |
| 7614310 | 7/1977 | Netherlands . |
| 8300284 | 2/1983 | PCT Int'l Appl. . |

OTHER PUBLICATIONS

Porter, S. C., et al., *The Effect of Choice of Process on Drug Release from Non-Pareils Film Coated with Ethylcellulose*, Proceed. Intern. Symp. Control. Rel. Bioact. Mater., 12, 41–42 (1985).

Baker, R., *Analysis of Oral Dosage Form Patents 1939 to 1985*.

*Primary Examiner*—Thurman K. Page
*Attorney, Agent, or Firm*—Venable, Baetjer, Howard & Civiletti

[57] ABSTRACT

The invention disclosed is amoxicillin microencapsulated granules with activity densities greater than about 0.200 g/ml. These granules are unusually small having diameters less than about 1000 microns. The granules optionally have a taste mask coating, and are particularly useful in hand-held flowable material dispensers. A process for manufacturing such granules is also disclosed.

32 Claims, No Drawings

AMOXICILLIN MICROENCAPSULATED GRANULES

BACKGROUND OF THE INVENTION

Over the past several years it has become obvious to health professionals and the pharmaceutical industry that optimal therapy with existing drugs has not been achieved with conventional dosage forms (e.g., tablets, capsules, injectables, suppositories) and dosing regimens. The term "optimal therapy" means the safest, most rapid, and most convenient amelioration of any particular disease state. Further, the "safety" of a dosage form or dosing regimen refers to the frequency and severity of side reactions. Improvement in therapy can then be defined as any change in the dosage form or regimen for an existing drug that: (1) reduces the frequency and severity of side reactions, (2) increases the rate at which cure or control is achieved, and (3) decreases the degree of disruption of normal patient activities.

In response to this growing perception, a number of novel drug delivery systems have been developed and brought to market. Some good examples are the transdermal delivery devices such as Nitro-Dur® (Key Pharmaceuticals), Nitro-Disc® (Searle), Transderm Nitro® (Ciba), Clonidine-TSS® (Boehringer-Ingelheim) and Transderm-Scop® (Ciba). Other examples are Theo-Dur® tablets, a sustained release form of theophylline, Theo-Dur Sprinkle® (U.S. Pat. 4,587,118) and Slo-Bid®. Theo-Dur Sprinkle® and Slo-Bid® are microencapsulated forms of slow release theophylline that are intended for use in pediatric patients or other patients who may have difficulty in swallowing a tablet. The microcapsules are supplied in hard gelatin capsules. The hard gelatin capsules are opened at the point of use by the care-giver and administered in a soft food.

This form of drug delivery has significant drawbacks. First, there are a small finite number of capsule sizes marketed, and this limits the physician's ability to prescribe an appropriate dose on the basis of a particular patient's weight, severity of disease, and therapeutic response. Second, there is the possibility of tampering which has become a subject of major concern related to the safety of over-the-counter pharmaceutical products.

Flowable material dispensers such as that described in U.S. Pat. 4,579,256 were developed to overcome these drawbacks. The Flowable Material Dispenser is an adjustable, metering and dispensing package. The dispenser can accurately deliver a granular pharmaceutical product to a patient by pouring the selected dosage onto a small quantity of soft food contained on a spoon prior to swallowing. The dispenser is child-resistant, protects the product from the surrounding environment and precisely delivers an adjustable dose well within the compendial requirements for uniformity of dosage units. However, microcapsules that are suitable for use in the Flowable Material Dispenser must meet certain narrow specifications with regard to average particle size, particle size distribution, shape and active agent concentration. These specifications are generally defined as follows:

| | |
|---|---|
| Particle size/size distribution (depending on dispenser design) | A: 710 Microns–1000 Microns<br>B: 590 microns–840 Microns<br>C: 500 microns–710 Microns |
| Activity density (potency & bulk density) | not less than 0.200 g/ml |
| Appearance | nearly spherical |
| Flow | freely flowing |

Although an acceptable product could be made beyond the limits of these parameters, high potency and small size are required to achieve the necessary bulk density which insures that the largest dose is contained in a volume that is convenient to swallow. Small size is also essential if the particles are to be relatively impalpable when added to soft food. High bulk density allows a dispenser of reasonable size for one hand operation to contain a ten to sixty day supply of drug. Narrow size distribution insures reproducibility of each measured dose and eliminates variation in bulk density due to segregation of sizes. This is critical to a device which measures solid particles by volume. Narrow particle size distribution also implies reproducibility of bulk density from batch to batch. Thus, the same volume will contain the same amount of drug every time in production, which is a new requirement, imposed by the flowable material dispenser but not by prior art delivery systems like hard gelatin capsules. It is also important that the microcapsules be nearly spherical to impart the flow characteristics that are required at every stage of assembly and use of the dispenser. The nearly spherical aspect of the microcapsules also enhances product elegance.

Presently available conventional pharmaceutically active granules are generally inappropriate for oral administration with semi-solid food or for use in a hand-held flowable material dispenser. These conventional granules are large and create a noticeable gritty mouthfeel for the patient. Large microgranule size also necessitates an increase in the smallest characteristic dimension of the measuring cylinder, and the flow channels of the flowable material dispenser if particle bridging is to be avoided. An increase in the smallest characteristic dimension of the measuring cylinder is also necessary if the requirements of the U.S. Pharmacopeia for Uniformity of Dosage Units are to be met. As those characteristic dimensions increase, so does the overall size of the flowable material dispenser. Each increase in size of the dispenser results in the loss of a degree of convenience in its use. At some microgranule size larger than 18 mesh (1000 microns), the flowable material dispenser becomes too large to be comfortably hand-held and hand-operated. Conventional granules are also difficult to accurately dispense from a hand-held flowable material dispenser due to the broad size distribution of granules both within and between batches, as well as the lack of uniform shape of the conventional granules.

Additionally, most pharmaceutically active agents have an unpleasant taste, and many such agents are administered to children who have more taste buds on their tongues than adults and are therefore more cognizant of unpleasant tastes (*Remington's Pharmaceutical Sciences*, 5th ed., p. 1226 (1975)). Some of the pharmaceutically active agents with a more notorious reputation for unpleasant taste include amoxicillin, dicloxicillin, ampicillin, penicillin, erythromycin, cephalosporins and prednisone.

Numerous attempts to mask these unpleasant tastes in conventional dosage forms such as tablets, solutions and suspensions follow the conventional wisdom of attempting to overpower the unpleasant flavor with a more pleasant one. For example, salty tastes are conventionally masked by syrups such as cinnamon syrup, orange syrup and cherry syrup; bitter tastes are conventionally masked by syrups such as cocoa syrup, raspberry syrup and cherry syrup; acrid or sour tastes are conventionally masked by syrups such as raspberry syrup and acacia syrup; and oily tastes are conventionally masked by syrups such as aromatic rhubarb syrup, compound sarsaparilla syrup and lemon syrup. These conventional taste-masking techniques were more often than not less than satisfactory, particularly in the case of children's medicines.

Amoxicillin is uniquely suited for incorporation into a flowable material dispenser because it is well known that dose-related gastrointestinal upsets (epigastric distress, nausea, vomiting, and especially diarrhea) occur commonly with amoxicillin administration. It is this adverse effect that the present invention is intended to eliminate. It is believed that much of the diarrhea that occurs during amoxicillin therapy is due to overdose and that accurate delivery of the appropriate dose by weight in taste-masked form will provide significant therapeutic advantage.

SUMMARY OF THE INVENTION

The present invention relates to pharmaceutically active microencapsulated granules comprising amoxicillin and a binder which have an unexpectedly high concentration (average activity density greater than about 0.200 g/ml), small size (less than about 1000 microns diameter), narrow size distribution, and uniformity of shape (spherical). A number of binders or combinations of binders may be used in the amoxicillin granules, including hydroxypropyl methylcellulose phthalate, cellulose acetate phthalate, polyvinyl acetate phthalate, polyvinylpyrrolidone, hydroxypropyl methylcellulose, polyethylene glycol, hydroxypropyl cellulose and polyethylene oxide. However, a preferred binder is a hydroxypropyl methylcellulose.

The granules preferably have a taste mask coating comprising a mixture of about 35% by weight to about 55% by weight ethylcellulose and about 45% by weight to about 65% by weight polyethylene glycol. The taste mask coating is applied to granules as a dispersion of the ethylcellulose/polyethylene glycol mixture in a solvent.

The granules are preferably manufactured by use of a fluidized bed technique which produces microencapsulated granules of uniform small size, uniform high concentration of amoxicillin, narrow range of size distribution and uniform spherical shape. Granules meeting these requirements are intended to be dispensed onto a food product, and therefore the taste mask coating performs its function by nullifying the unpleasant taste of the pharmaceutically active agent rather than by overpowering the unpleasant taste as is attempted with conventional taste masking techniques. With the granules of the present invention, the patient tastes only the food product because the unpleasant taste of the amoxicillin has been nullified by the taste mask coating.

DETAILED DESCRIPTION OF THE INVENTION

The invention relates to amoxicillin microencapsulated granules with activity densities greater than about 0.200 g/ml. Preferably, the activity density of the amoxicillin microgranules is about 0.320 g/ml to about 0.360 g/ml. Activity density is the product of the granule potency multiplied by its bulk density.

Such granules are particularly useful in flowable material dispensing devices. One such dispensing device is the "Flowable Material Dispenser" disclosed in U.S. Pat. 4,579,256 incorporated herein by reference.

In order for pharmaceutically active granules to be used in the above-described dispenser, such granules must exhibit a high concentration of pharmaceutically active agent, a small size, a narrow size distribution and a uniformity of shape, preferably spherical. They must also be resilient enough to withstand packaging on high speed filling equipment and shipment throughout the world. The uniformly spherical granules ensure the accuracy and reproducibility of doses from the dispenser. The properties of high concentration and small size are necessary for convenience of administration by minimizing the amount of granules the patient has to swallow. The high concentration and small size, along with the narrow size distribution of uniformly spherical granules are also desirable so that the granules do not create an unpleasant gritty feeling in the patient's mouth when the granules are ingested with the food on which they are dispensed. Small average size is also necessary if the flowable material dispenser is to be kept small enough overall to be hand-operated.

In general, the granules comprise an inert seed which has a pharmaceutically active coating applied thereto to make a pharmaceutically active seed. A taste mask coating is applied to the pharmaceutically active seed in a preferred embodiment.

Pharmaceutically active seeds comprise inert seeds to which a pharmaceutically active coating has been applied. Commonly used inert starting seeds on which the active coating composition is applied include nonpareil seeds, sucrose crystals, silica gel and ion exchange resins. The preferred size range for inert starting seeds is inversely related to the average daily dose of the drug in question. In the case of high dose drugs like amoxicillin, it is desirable to start with the smallest seed possible to obtain the greatest finished drug content. This minimizes the total volume of microcapsules that must be ingested. However, the difficulty encountered in coating discrete seeds smaller than 175 microns increases dramatically. A 60/80 mesh (177 microns–250 microns) starting seed represents the smallest size that can be dealt with without using extraordinary measures. If drug crystals or granulation are to be used as the starting material rather than an inert seed, the preferred starting size would be between 25 and 40 mesh (about 420 microns to about 700 microns). The larger seed size serves to reduce the time required to apply additional drug to the seeds to meet the finished product seed size requirements of diameters less than 1000 microns. Usually, drug crystals or granulation of large size and suitable physical strength are not available on the open market for use as starting materials. Therefore, inert starting seeds are most commonly used in the present invention.

The size of the finished granule is less than about 18 mesh (less than about 1000 microns diameter) and a preferred size is between about 18 mesh and about 25 mesh (about 710 microns to about 1000 microns diameter). The preferred starting seeds for the amoxicillin microgranules are (60/80 mesh) sucrose crystals. The 25/30 nonpareil seeds are usually used with drugs which require lower daily doses, and the 60/80 sucrose crystals are usually used with drugs which require a higher daily dose.

The pharmaceutically active coating applied to the inert starting seed comprises a mixture of amoxicillin or one of its pharmaceutically active salts and a binder. The ratio of amoxicillin to binder is in the range of about 5:1 to about 13:1. The mixture commonly comprises about 83% by weight to about 93% by weight amoxicillin and about 7% by weight to about 17% by weight binder.

Suitable binders for use in the pharmaceutically active coating are conventional binders such as hydroxypropyl methylcellulose, hydroxypropyl methylcellulose phthalate, polyvinylpyrrolidone, polyethylene oxide, polyethylene glycol, hydroxypropyl cellulose, cellulose acetate phthalate, polyvinyl acetate phthalate and mixtures thereof. A preferred binder is hydroxypropyl methylcellulose.

The active coating is applied to the inert starting seed as an active coating composition comprising the amoxicillin/binder mixture dispersed in a solvent. Suitable solvents include acetone, water, ethanol, methanol, isopropanol, chloroform, methylene chloride, methyl ethyl ketone, ethyl acetate, carbon tetrachloride, benzene and combinations thereof. Any number of these solvents may be combined to achieve the proper balance between solubility of binder and dispersion of amoxicillin while still maintaining a pumpable and sprayable viscosity. Such a desired viscosity is between about 5 cps and about 100 cps as measured by Brookfield ® viscometer or suitable equivalent instrumentation. A preferred solvent is a mixture of about 68% by weight to 88% by weight acetone and about 12% by weight to about 32% by weight water.

A taste mask coating may be applied to the active seed. Such a taste mask coating preferably comprises a mixture of ethylcellulose and polyethylene glycol. The ethylcellulose is present as about 35% by weight to about 55% by weight of the mixture, and the polyethylene glycol is present as about 45% by weight to about 65% by weight of the mixture. A preferred taste mask coating comprises a mixture of about 45% by weight ethylcellulose and about 55% by weight polyethylene glycol.

Ethylcellulose is an ethyl ether of cellulose commercially available from Dow Chemical Company as Ethocel ® Commercially available ethylcellulose generally has an ethoxy content of about 43% to about 50%. Medium-type viscosity grade ethylcellulose contains about 45%–47% ethoxy groups, whereas standard-type viscosity grade ethylcellulose contains about 48%–49.5% ethoxy groups. A preferred ethylcellulose is a standard-type with a nominal Ubbelohde viscosity of about 10 cps for a 5% by weight solution (in 80% toluene and 20% ethanol) measured at about 25° C. This preferred ethylcellulose (Ethocel Std. 10) softens at about 140° C. (284° F.) and is soluble in solvents such as ethyl acetate, ethylene dichloride, benzene, toluene, xylene, butyl acetate, acetone, methanol, ethanol, butanol and carbon tetrachloride. Ethylcellulose is generally prepared from wood pulp or chemical cotton by treatment with alkali and ethylation of the alkali cellulose with ethyl chloride.

Polyethylene glycol is a polymer resin which has the formula:

where n is greater than or equal to 4, and generally ranges between 4 and about 210. Polyethylene glycol may be prepared by reacting ethylene glycol with ethylene oxide in the presence of sodium hydroxide (NaOH) at temperatures in the range of 120° C. (248° F.) to 135° C. (275° F.) under a pressure of about 4 atmospheres. Depending on its molecular weight, polyethylene glycol may be a clear viscous liquid or a white waxy solid at room temperature.

Polyethylene glycol with molecular weights between about 190 and about 900 are viscous liquids, while those with molecular weights of about 1000 to about 9000 are waxy solids. The viscosity of polyethylene glycol is measured at 99° C. (210° F.) and ranges from about 4.3 centistokes to about 900 centistokes. The freezing point of polyethylene glycol ranges from about 4° C. (39° F.) to about 63° C. (145° F.). As the molecular weight of polyethylene glycol increases its water solubility, vapor pressure, hygroscopicity, and solubility in organic solvents decreases, and its freezing or melting range, specific gravity, flash point and viscosity increases. Polyethylene glycol is readily soluble in aromatic hydrocarbons and only slightly soluble in aliphatic hydrocarbons.

Suitable polyethylene glycols are those with molecular weights between about 1000 and about 9000. A preferred polyethylene glycol is that classified as polyethylene glycol 8000, which is available from Union Carbide under the trademark Carbowax ®. This preferred polyethylene glycol has an average molecular weight of about 8000, a viscosity between 470 and 900 centistokes, and a melting range between about 60° C. (140° F.) and 63° C. (145° F.).

The ethylcellulose (Ethocel Std. 10)/polyethylene glycol 8000 mixture which comprises the taste mask coating is preferably applied to the active seeds as a composition comprising a dispersion in a solvent. Suitable solvents for the dispersion include those listed above or any combination thereof in which ethylcellulose is soluble and in which polyethylene glycol is soluble. A preferred solvent is a mixture of about 75% by weight to about 95% by weight acetone and about 5% by weight to about 25% by weight water. When dispersed in the solvent, the ethylcellulose (Ethocel Std. 10)/polyethylene glycol 8000 mixture is preferably present as about 5 by weight of the dispersion.

The potency of the finished amoxicillin microencapsulated granule is about 650 mg/g to about 750 mg/g. This potency range permits the delivery of a reasonable number of granules per desired therapeutic dosage. A therapeutic dose of amoxicillin microencapsulated granules is preferably dispensed onto a patient's food, and should be of a small enough quantity so that the dose is a minor percentage of the quantity of food.

An additional requirement of the finished granules is that they be of a uniformly small size, less than about 1000 microns diameter. The finished granules preferably have sizes from about 18 mesh (1000 microns diameter) to about 25 mesh (710 microns diameter). The uniformly small size is undetectable by mouthfeel when the patient consumes the food on which the granules are dispensed. Larger granules tend to create a noticeable gritty mouthfeel when consumed with food.

The uniformly small size of the finished granules is also necessary for use of the granules in a reasonably sized hand-held dispenser. Such hand-held dispensers are the preferred method for dispensing therapeutic doses of amoxicillin microencapsulated granules. Finished granules dispensed from a hand-held dispenser are also preferably of a uniformly spherical shape and have a narrow size distribution to insure uniformity of dose.

The preferred characteristics of uniform small size, uniform spherical shape, narrow size distribution and high concentration of amoxicillin are achievable by using a rotor granulator in the manufacture of the amoxicillin microencapsulated granules. Conventional fluidized beds such as Wurster columns or fluid bed granulator/dryers may also be used to manufacture the amoxicillin microencapsulated granules.

In general, a rotor granulator comprises a processing chamber with a rotor at its lower portion. Air is introduced at the level of the rotor for fluidization of the product bed in two ways. Air may enter the chamber through the opening between the rotor and the stator and through a second opening about midway across the radius of the rotor. This introduction of air results in a spiral and twisting air pattern within the chamber. When the inert seeds are introduced into the chamber and coated, the combination of the spinning rotor and the air circulation pattern is purported to provide seeds with higher individual densities that are rounder and smoother than those produced in conventional fluidized bed systems such as Wurster columns and Glatt fluidized bed granulator/dryers.

Once the starting seeds have been fluidized in the rotor granulator, the suspension of binder and amoxicillin is introduced through spray guns mounted in the periphery of the stator near the bottom of the product chamber or near the top of the product chamber to spray on the product from above. Although the starting seeds could also be coated using conventional fluidized beds, the rotor granulator is purported to produce a more evenly coated product with a higher concentration of amoxicillin and a uniformity spherical shape.

When used to manufacture amoxicillin microencapsulated granules with a taste mask coating, inert starting seeds are first fluidized in the rotor granulator. The active coating composition is then applied to the inert starting seeds by spray nozzles, preferably located along the inner circumference of the rotor granulator, to produce pharmaceutically active seeds. When the active seeds have acquired the desired potency, they are dried at about 30° C. (86° F.) in the rotor granulator until a stable product temperature is obtained.

The taste mask coating composition is then applied to the active seeds which are fluidized in the rotor granulator. The taste mask coating composition is applied by spraying through the same nozzles used to spray the pharmaceutically active coating. After the desired amount of taste mask coating has been applied, the finished amoxicillin microencapsulated granules are dried in the rotor granulator at about 35° C. (95° F.) until a stable product temperature is obtained. These finished granules will have the preferred uniform small size (less than about 1000 microns diameter), the uniform spherical shape, narrow size distribution an the preferred concentration (activity density greater than about 0.200 g/ml).

Despite the purported benefits of the rotor granulator, it has been found that conventional fluidized bed techniques produce amoxicillin microencapsulated granules which meet all of the requirements for use in a hand-held flowable material dispenser. Such fluidized bed techniques are well known to those skilled in the pharmaceutical manufacturing art. With regard to the present invention, fluidized bed techniques are the preferred method of manufacture for amoxicillin microencapsulated granules.

An additional optional step after the microencapsulated granules have been dried is the addition of an antistatic agent. About 0.75% by weight, of the final product weight, of a suitable antistatic agent is added to the fluidized bed or rotor granulator after the final drying step. The fluidized bed is run for about five minutes to distribute the antistatic agent onto the microencapsulated granules. This amount of antistatic agent is sufficient to coat the granules and prevent the granules from sticking to the sides of the flowable material dispenser. The prevention of adherence between the granules and the dispenser serves to reduce variability in dosing which is more common when an antistatic agent is not used.

Suitable antistatic agents include silicon dioxide, polacrilin, talc, magnesium stearate, calcium stearate, stearic acid and combinations thereof. The preferred antistatic agent is silicon dioxide. Silicon dioxide, unlike many of the other suitable antistatic agents, serves the dual purpose of being a moisture scavenger. The elimination of the excess moisture which usually develops from condensation due to climatic changes during shipping and storing, also aids in eliminating variable dosing problems and flow problems with the granules.

The finished amoxicillin microgranules may be used in a variety of dosage delivery systems, including tablets, capsules and flowable material dispensers. When used in a tablet delivery system, the amoxicillin microgranules are compressed or formed into a tablet using conventional pharmaceutical tabletting techniques. When used in a capsule delivery system, the amoxicillin microgranules are used to fill water soluble capsules using conventional pharmaceutical capsule manufacturing techniques. When used in a flowable material dispenser delivery system, the amoxicillin microgranules are used to fill the flowable material dispenser.

The features and advantages of the invention are further demonstrated by the following examples. In this specification and in the following examples, all parts and percentages are expressed by weight on an as-is basis, and all temperatures are expressed in degrees Centigrade unless expressly stated to be otherwise.

EXAMPLE 1

Preparation of Amoxicillin Microencapsulated Granules

A 7.65% (w/w) binder dispersion was formed from 126.6 grams hydroxypropyl methylcellulose 2910, USP in 1528.2 grams acetone. This dispersion was then mixed with 431.0 grams purified water, USP, to form a clear solution. The clear solution was then mixed with 928.4 grams of amoxicillin trihydrate, and the mixing continued for about 10–15 minutes until a lump-free active coating composition was formed.

The active coating composition was applied (sprayed) onto 500 grams of sucrose USP (starting seeds) to form active seeds. The starting seeds were 60/80 mesh size. The application of the coating composition took place after the sucrose was fluidized in a Vector Freund Spir-A.-Flow ® rotor granulator. After all of the active coating composition had been applied, the active seeds were dried at approximately 35° C. (95° F.) for about 20 minutes until a stable product temperature of 31° C. (87.8° F.) was obtained. The dried active seeds were discharged into a suitable container and labelled Amoxicillin Active I Seeds.

A portion (500 grams) of the Active I Seeds were returned to the Spir-A-Flow ®. A second active coating composition was prepared as described above and applied (sprayed) onto the Active I Seeds. The product was dried as described above, discharged into a suitable container and labelled Amoxicillin Active II Seeds.

A portion (500 grams) of the Active II Seeds were returned to the Spir-A-Flow ®. A third active coating composition was prepared as described above and sprayed onto the Active II Seeds. The product was dried as described above, discharged into a suitable container and labelled Amoxicillin Active III Seeds. The tubing used to spray the active coating composition was then rinsed with acetone.

A taste mask coating composition was then prepared by first forming a solution of 16.9 grams ethylcellulose (Ethocel Std. 10) in 605.6 grams acetone. To this solution was added 20.6 grams polyethylene glycol 8000 NF. Finally, 106.9 grams purified water was added and the solution was allowed to mix for about 5 minutes until a translucent taste mask coating composition was formed.

The taste mask coating composition was applied to a portion (500 grams) of the Active III Seeds which were fluidized in the rotor granulator. After all of the composition was applied, the taste mask coated microencapsulated granules were dried in the rotor granulator at approximately 35° C. (95° F.) for about 30 minutes until a stable product temperature of 32° C. (89.6° F.) was obtained.

Finally, 9.5 grams of silicon dioxide NF were added to the dried fluidized granules in the rotor granulator. The rotor granulator was run for about five minutes, after which time the granules were coated with the silicon dioxide. These seeds were then discharged into a suitable container and labelled Amoxicillin Taste Masked Seeds.

Table 1 below shows the amounts of each ingredient in the final product.

TABLE 1

| Quantity per 250 mg dose of amoxicillin base (mg) | Ingredient | Quantity per kg batch size (g) |
| --- | --- | --- |
| 294* | Amoxicillin, USP | 819* |
| 40.1 | Hydroxypropol Methylcellulose 2910, USP | 112 |
| 11.5 | Sucrose, USP | 32.0 |
| 4.81 | Ethylcellulose 10, NF | 13.4 |
| 5.89 | Polyethylene Glycol 8000, NF | 16.3 |
| 2.69 | Silicon Dioxide, NF | 7.5 |
| 657** | Acetone, NF | 1829** |
| 167** | Purified Water, USP | 465** |

*Based on theoretical activity of 85%. The actual weight of amoxicillin trihydrate used is calculated on a lot-to-lot basis according to the following formula:

$$\text{actual amount of amoxicillin trihydrate to charge} = \frac{\text{theoretical amount to charge} * (85\%)}{\text{measured activity } (\%)}$$

**Removed during processing.

EXAMPLE 2

Preparation of Microgranules of Amoxicillin with Polyvinyl-pyrrolidone as a Binder Active I stage microencapsulated granules were prepared (820408A) in accordance with Example 1 above. However, the active coating composition was composed of 3.5% (w/w) PVP K-30, 31.5% (w/w) amoxicillin, 32.5% (w/w) water and 32.5% (w/w) Methyl Alcohol. The starting seeds used were 40/60 mesh nonpareils. The batch ran very well and the product was 89% usable material (good material in the proper size range). However, this system's reproducibility was poor. After failing on eight attempts to obtain a second successful batch with this system, this binder system was not pursued further at the Active I level. However, since there was one good run, the seeds of that run were carried forward to the Active II stage. This system became even more difficult to process at the Active II stage and therefore this binder system was not pursued further. It is possible that alteration of the processing conditions or the solvent system could improve the results so that a product of this nature might be deemed acceptable.

EXAMPLE 3

Preparation of Microgranules of Amoxicillin with Hydroxypropyl Methylcellulose as a Binder An attempt was made to prepare Active I stage microencapsulated granules (820413A) in accordance with Example 1 above using HPMC E-15LV as the binder at levels of 6.25 by weight and 9.9% by weight. The initial run (lot #870413A) at 6.25% and a solids concentration of 35% in a mixture of equal parts of water and methyl alcohol was not sprayable because the slurry was too thick. After lowering the solids concentration to 25%, a sprayable dispersion was obtained. At this concentration, neither binder level was sufficient. Both powder and agglomerates were obtained in high amounts during the runs. The higher binder level (9.9%) did not help the powder problem and the lower level (6.25%) did not improve the oversize problem. It is possible that alteration of the processing conditions or the solvent system could improve the results so that a product of this nature might be deemed acceptable.

EXAMPLE 4

Process Parameters and Usable Yield for Amoxicillin Active I Seeds

Following the process described in Example 1 above, various size batches of Amoxicillin Active I Seeds were produced using a rotor granulator run at varying rotor speeds, spray rates and batch sizes. The other rotor granulator parameters, set forth below, were kept constant at the designated values: atomization air rate (45 LPM); atomization air pressure (1.5 bar); slit air (26 LPM); fluid air (5 LPM); and inlet air temperature (30° C., 86° F.). With all but one batch, the starting spray rate was 5 g/min. and the ending spray rate was 13 g/min., but the time to reach a spray rate of 8 g/min. was varied.

Table 2 below sets forth the results from the different batches in terms of total yield from the rotor granulator, usable yield (microencapsulated granules which meet the required particle size specifications for the first build-up of active seeds, i.e. are between 30 mesh and 60 mesh in size), and amount of powder produced (part of the unusable yield).

TABLE 2

| Lot # | Batch Size (g) Starting | Batch Size (g) Finished Product | Rotor Speed (rpm) | Elapsed Time to 8 g/min (min) | Total Yield (%) | Usable Yield (%) | Amount of Powder (g) |
|---|---|---|---|---|---|---|---|
| 870508A | 500 | 1415 | 250 | 6 | 91.0 | N/A | 75.0 |
| 870509A | 500 | 1415 | 200–265 | 0 | 90.2 | 58.6 | 21.2 |
| 870511A | 500 | 1415 | 250 | 31* | 93.2 | 83.1 | 33.4 |
| 870604A | 500 | 1415 | 200–400 | 56 | 95.6 | 86.7 | 21.0 |
| 870615A | 500 | 1555 | 400 | 80 | 96.3 | N/A | 24.0 |
| 870915A | 500 | 1555 | 400–475 | 46 | 92.4 | 88.2 | 38.3 |
| 870921A | 500 | 1555 | 400–475 | 115 | 91.2 | 83.3 | 49.0 |
| 870626A | 500 | 1866 | 400 | 120 | 93.0 | 45.1 | 26.8 |
| 870908A | 500 | 1866 | 400 | 96 | 91.9 | 59.7 | 30.4 |

*This run was started at a spray rate of 7 g/min.

It was found that when the seeds were at their smallest size (when being built up to the Active I stage as set forth above), small forces of attraction were sufficient to hold them together and cause unacceptable agglomeration. Any rapid increase in spray rate increased these forces and agglomerates formed. A small amount of powder combined with a small amount of solvent/binder also went a long way toward increasing the forces of attraction at small seed sizes and to the formation of agglomerates.

This tendency to agglomerate when the seed size is small can be somewhat countered by improving the movement of the seeds within the fluidized bed (i.e., improving the flow pattern). Increasing "power input" to the bed by increasing the rotor speed, and/or the volume of fluidizing air (changing the "power variables") creates a less ordered flow pattern. At small seed sizes, any increase in the levels of the "power variables" seems to result in a visually less ordered, more desirable flow pattern. This less ordered flow closely resembles the flow pattern seen at "normal" levels of the power variables with larger seeds. Additionally, agglomeration can be reduced by avoiding a rapid increase in the spray rate in the early stages of a run, and/or avoiding excess powder formation. The importance of the rate of increase in spray rate is seen in Table 2. Shorter elapsed time to a spray rate of 8 g/min gives a lower usable yield at all batch sizes except the largest. This example begins to show the unique combination of ingredients and processing conditions represented by the invention.

EXAMPLE 5

Usable Yields—Buildup of Amoxicillin Active II Seed

Active seeds from Example 4 above were subjected to a second buildup process wherein additional active coating was applied using a rotor granulator as explained in Example 1 above. As in Example 4, the rotor speeds and time to reach a spray rate of 8 g/min. were varied. Usable yield was determined by the amount of granules which were of a size between 20 mesh and 40 mesh. The results of this second buildup are set forth below in Table 3.

TABLE 3

| Lot # | Batch Size (g) Starting | Batch Size (g) Finished Product | Rotor Speed (rpm) | Elapsed Time to 8 g/min (min) | Usable Yield (%) |
|---|---|---|---|---|---|
| 870511B | 500 | 1415 | 250–320 | 8 | 88.9 |
| 870512A | 500 | 1415 | 250–300 | 30 | 90.6 |
| 870627A | 600 | 1866 | 400 | 120 | 79.9 |
| 870909A | 600 | 1866 | 400–475 | 45 | 92.0 |
| 870916B | 500 | 1555 | 400–450 | 36 | 93.4 |

TABLE 3-continued

| Lot # | Batch Size (g) Starting | Batch Size (g) Finished Product | Rotor Speed (rpm) | Elapsed Time to 8 g/min (min) | Usable Yield (%) |
|---|---|---|---|---|---|
| 870921C | 500 | 1555 | 400–450 | 40 | 93.5 |

During build-up of the Active II Seeds, it was observed, given a constant power input, that flow pattern improved (became less ordered) as the size of the seeds grew. Assuming that the attractive force caused by powder and solvent/binder is the same as in the case of the Active I Seed build-up, it was not strong enough to cause agglomeration. Apparently, for the "normal" levels of the power variables, a seed size exists at which the flow pattern is optimum. When the seeds travel in this pattern they resist agglomeration.

EXAMPLE 6

Usable Yields—Buildup of Amoxicillin Active III Seed

Active II Seeds from Example 5 above were subjected to a third buildup process wherein additional active coating was applied using a rotor granulator as explained in Example 1 above. As in Examples 4 and 5, rotor speeds and time to reach a spray rate of 8 g/min. were varied. Usable yield was determined by the amount of granules which were of a size between 18 mesh and 30 mesh. The results of this third buildup are set forth in Table 4 below.

TABLE 4

| Lot # | Batch Size (g) Starting | Batch Size (g) Finished Product | Rotor Speed (rpm) | Elapsed Time to 8 g/min (min) | Usable Yield (%) |
|---|---|---|---|---|---|
| 870513A | 500 | 1415 | 250–320 | 16 | 85.4* |
| 870512B | 500 | 1415 | 250–310 | 31 | 81.8* |
| 870528A | 500 | 1415 | 250–275 | 45 | 87.9 |
| 870629A | 600 | 1866 | 400 | 152 | 69.0 |
| 870629B | 600 | 1866 | 400 | 120 | 67.9 |
| 870910B | 600 | 1866 | 400–475 | 46 | 69.6 |
| 870917 | 500 | 1555 | 400–475 | 34 | 83.1 |
| 870922B | 500 | 1555 | 400–450 | 51 | 80.5 |

*Usable yield does not reflect a considerable amount of undersize present which could be processed further and brought into the proper size range and therefore could be considered usable.

In the beginning of the build-up of Active II Seeds to Active III Seeds, the flow pattern remained optimal as in Example 5, however, as the seeds grew in mass the pattern degenerated Further increases in seed mass caused the pattern to degenerate to a point where the bed "sat" on the rotor. This allowed the attractive forces to effectively increase, causing agglomeration.

In order to minimize the attractive forces and resulting agglomeration, the power input to the seeds should be continually increased throughout the run. This will, in effect, aid in keeping the seeds traveling in the optimum flow pattern thereby holding the forces of attraction to a minimum. In the absence of a continual power increase, it would then be necessary to stop the run before the seeds reach a size where they begin to "sit down" and the optimum pattern degenerates. Any rotor granulator has a capacity above which, at maximum power inputs, seed movement is restricted. A run should be stopped before this point is reached.

EXAMPLE 7

Preparation of Immediate Release, Taste Mask Coated Amoxicillin Microgranules Using Ethylcellulose Active III seeds (18/30 mesh) that were manufactured as described in Example 1 above were used in a series of experiments aimed at obtaining a final coating that produced an immediate release, taste masked product. The first systems investigated used Aquacoat ECD-30, an aqueous dispersion of ethylcellulose. This material was combined with HPMC E-5 and triethylcitrate (TEC), a plasticizer, in a 45/45/10 w/w mixture (870526A and B). The final coating level in this experiment was 10% by weight. The dissolution of the active pellets coated with this system was very good (100% released in 10 minutes), and the characteristic penicillin flavor was well masked. However, a large amount of agglomerates were generated during processing.

In an attempt to decrease the oversized material but not affect the release rate, the plasticizer of the system mentioned above was changed to Myvacet (870527A, 27B, 29A and 29B). The ratios of the materials used in this system were the same as those described above. This change in plasticizer did not significantly lower the level of agglomerates being produced, but the pellets still dissolved rapidly and showed satisfactory taste mask characteristics. With both systems using Aquacoat, there was a large amount of static electricity present in the rotor granulator during the run. The static electricity seemed to draw the pellets together in loose aggregates which were wetted with coating solution and ultimately agglomerates formed Apparently, an inherent property of the aqueous ethylcellulose was causing the undesirable electrical charge when it was processed in the rotor granulator. It is believed that further experimentation with process conditions, and anti-static agents would allow Aquacoat to be used a taste mask film former for amoxicillin microencapsulated granules.

EXAMPLE 8

Preparation of Immediate Release, Taste Mask Coated Amoxicillin Microgranules Using Ethylcellulose and Polyethylene Glycol Active III seeds (18/30 mesh) that were manufactured as described in Example 1 above were used in a series of experiments using combinations of ethylcellulose (Ethocel Std. 10) and polyethylene glycol (PEG) as an immediate release, taste mask coating. This was a novel use of these ingredients since ethylcellulose is normally thought of for use in sustained release applications.

It was hypothesized that a water soluble material would concentrate in discrete domains in the finished film. These water soluble domains would dissolve away when contacted by dissolution medium in an in-vitro release test or by bodily fluids after ingestion. This would leave "holes" in the film coat through which drug could be released. The ethylcellulose portion would serve as the primary taste masking material The lowest molecular weight PEG available (PEG 400) was selected because it was believed that it would have less of a tendency to form an insoluble interpenetrating network, creating a slow release dissolution pattern and defeating the purpose of the coating. The polymers were dissolved in acetone at a concentration of 5% with an Ethocel/PEG 400 ratio of 80/20 (w/w). A 5% by weight coating was applied. The product was well taste masked but dissolution profiles showed that only 6% of the drug was released after 90 minutes in water (870611A). (The optimal profile of an immediate release product should show 100% released in 90 minutes or less).

Subsequent experiments used 60% and 50% Ethocel T-10 (870611B; 870612B) in an attempt to improve the release rate by increasing the water soluble portion. Satisfactory release rates could only be obtained at low coating levels (1%). Process times using these low coating levels and a reasonable spray rate were considered to be too short. Short process times do not insure an even, homogenous coat across the pellet surface. The coat weight sensitivity exhibited by this coating system was more consistent with films of pure ethylcellulose than with mixtures of ethylcellulose and water soluble polymers.

Since PEG 400 had not given satisfactory release rates at reasonable coating levels, it was hypothesized that an even lower molecular weight material would yield satisfactory release rates. It was thought that propylene glycol (PG) could be considered a very low molecular weight polyethylene glycol and that this when coupled with the Ethocel T-10 would provide an adequate film former. Various Ethocel T-10/PG ratios were used but once again acceptable release rates were achieved only at low coating levels. A more dramatic decrease in release rate was seen as the coating level was increased than was seen with the PEG 400 (870611C, 870612A).

A further experiment (870616B) was run using a higher molecular weight polyethylene glycol. The system used was Ethocel T-10 and PEG 1450 in equal amounts, by weight. Active III pellets were coated with this system to levels similar to the ones used in the PG and PEG 400 experiments. The dissolution results for this system (67% released in 90 minutes) were superior to those of prior Ethocel systems, and the characteristic penicillin taste was well masked. Since an improvement in the release rate was unexpectedly seen when the molecular weight of the PEG was increased from 400 to 1450, it was postulated that further increases in molecular weight might produce even better release rates.

Two more sets of experiments were conducted with PEG molecular weights of 4500 and 8000. Dissolution profiles of the products obtained from these experiments substantiated the belief that as the molecular weight of the PEG is increased, the release rate of the drug is accelerated. It was decided, after further confirmatory work, that the product with the best taste, dissolution profile and manufacturability had been obtained when a solution with equal amounts of Ethocel (T-10) and PEG (8000) was used to coat active pellets to a level of 3% (870623A, 870618A, 870618B, 870622A, 870622B). Since weighing variations could occur at the manufacturing level, a decision was made to test the effects on the final product (relative to taste and dissolution) if a 10% overage of either the ethylcellulose or the polyethylene glycol was added to the coating solution. Dissolution results of pellets coated with a 3% taste mask solution using a 60/40 ratio (Ethocel/PEG) were much too slow (870623B) in comparison to the results of a 3% coat with a 50/50 ratio. The product coated with 3% of a 40/60 solution (870708B) showed a release pattern equivalent to the 50/50 product. However, the increase in the water soluble portion of the coating caused an insufficient masking of the amoxicillin taste.

Since the allowable degree of deviation from the optimum solution (50/50) was unknown, a decision was made to hedge toward possible taste mask failure (not enough Ethocel) rather than dissolution failure (too much Ethocel) in the event that weighing variations did take place during manufacturing. Thus, a target ratio of 45/55, Ethocel (T-10) to PEG (8000), was established. A significant variation in solution preparation would have to occur to produce a product with an unacceptable dissolution profile. Batches made at this level showed satisfactory taste mask characteristics and rapid dissolution (870915B).

EXAMPLE 9

Pharmacokinetic Data

Amoxicillin microencapsulated granules which were prepared in accordance with Example 1 above were compared to a commercially available amoxicillin capsule formulation (Amoxil®—Beecham Laboratories) and a commercially available amoxicillin suspension (Amoxil®) to determine relative bioavailability.

Twenty-one subjects were administered a single dose (500 mg) of each formulation in a randomized, crossover format with each dose separated by a 7-day washout period.

Subjects were healthy male and female volunteers, 21 to 39 years of age, and weighed within 10% of ideal body weight. Subjects were determined healthy by physical examination, medical history, and laboratory tests. Females had negative serum pregnancy tests and were either surgically sterile or using a reliable method of contraception.

Subjects were administered the amoxicillin formulation with one teaspoonsful of applesauce and 180 ml of water.

Five (5) milliliters of blood were collected prior to amoxicillin administration, and then at 0.5, 0.75, 1.0, 1.25, 1.5, 2.0, 3.0, 4.0, 5.0, 6.0, 8.0, and 10.0 hours after administration. The blood was allowed to clot. Serum was separated by centrifugation within 60 minutes after collection. A seraclear filter was used to clarify the serum. Serum was placed in labelled polypropylene tubes and stored frozen at −20 ° C.

Amoxicillin concentrations were determined by microbiological assay using *Bacillus subtilus* spores. An agar well procedure was performed in 150 mm plates containing Antibiotic Media #1 (Difco®), adjusted to pH 6.5 before sterilization.

The mean pharmacokinetic parameters for each amoxicillin formulation are presented below in Table 5A.

TABLE 5A

|  | Microencapsulated Granules | Amoxil Suspension | Amoxil Capsule |
|---|---|---|---|
| $C_{max}$ | 4.70 ± 1.06 | 5.27 ± 1.51 | 4.73 ± 1.19 |
| $T_{max}$ | 1.45 ± 0.42 | 1.18 ± 0.42 | 1.70 ± 0.95 |
| Ke | 0.615 ± 0.111 | 0.597 ± 0.098 | 0.648 ± 0.084 |
| Half-Life | 1.16 ± 0.22 | 1.19 ± 0.20 | 1.09 ± 0.13 |
| $AUC_{0-10}$ | 13.61 ± 2.64 | 12.77 ± 2.64 | 14.20 ± 3.25 |
| $AUC_{0-\infty}$ | 13.85 ± 2.67 | 13.00 ± 2.62 | 14.45 ± 3.27 |

A paired t-test was used to compare the microencapsulated granule formulation of the present invention to the Amoxil® suspension, and the microencapsulated granule formulation of the present invention to the Amoxil® capsule. P values are provided below in Table 5B.

TABLE 5B

|  | Microencapsulated Granules to Suspension | Microencapsulated Granules to Capsule |
|---|---|---|
| $C_{max}$ | 0.238 | 0.907 |
| $T_{max}$ | 0.011 | 0.195 |
| Ke | 0.608 | 0.342 |
| Half-Life | 0.708 | 0.234 |
| $AUC_{0-10}$ | 0.093 | 0.381 |
| $AUC_{0-\infty}$ | 0.088 | 0.385 |

Differences were evaluated with $\alpha=0.05$. There were no differences in bioavailability between the microencapsulated formulation of the present invention compared to the Amoxil® suspension, or the Amoxil® capsule. The only statistically significant difference was found with $T_{max}$ of the microencapsulated granule formulation of the present invention compared to the Amoxil® suspension. The mean $T_{max}$ of the microencapsulated granules formulation was 1.45 hours, compared to 1.18 hours for the Amoxil® suspension. The $T_{max}$ for the capsule formulation was 1.79 hours.

The microencapsulated granule formulation of the present invention was equivalent to the Amoxil® capsules and suspension in terms of bioavailability. The small differences in mean pharmacokinetic parameters (only $T_{max}$ was significant) is unlikely to be clinically important.

EXAMPLE 10

Stability of Amoxicillin Microencapsulated Granules

Five batches of amoxicillin microencapsulated granules were prepared in accordance with Example 1 (Batches 870923C-2, 870630A-1, 870915B-2, 870923B-1 and 870923C-1). After manufacture, finished microgranules of each batch were sealed in a prototype of hiMedics, Inc.'s Flowable Material Dispenser (U.S. 4,579,256). Stability was determined following storage at room temperature and at elevated temperature. The stability data for each batch (870923C-2, 870630A-1, 870915B-2, 870923B1 and 870923C-1) is presented below in Tables 6A, 6B, 6C, 6D and 6E, respectively.

TABLE 6A

STORAGE CONDITIONS

Lot #: 870923C-2  Theoretical Potency (mg/g): 702.0

| Parameter & Method | Initial | 3M RT | 6M RT | Specifications |
|---|---|---|---|---|
| Potency (mg/g) | 671.5 | 683.4 | 675.3 | 629.0–839.0 mg/g |
| Potency (% of Theory) | 95.7 | 97.4 | 96.2 | |
| Potency (% of Initial) | 100.0 | 101.8 | 100.6 | 90.0–120.0% LC |
| Loss of Dryness (% w/w) | 0.60 | 0.83 | 0.63 | Report value |
| Water (%) | 12.55 | 12.48 | 11.60 | Report Value |
| Appearance | Pass | Pass | Pass | White to Off White Free Flowing, Uniform Spheres |
| Color | N/A | N/A | N/A | Report Value |
| Odor | Pass | Pass | Pass | Compares to Standard |
| Taste | Pass | Pass | Pass | None to Slight Bitter |
| Bulk Density (g/ml) | 0.488 | 0.490 | 0.504 | Report Value |
| Dissolution, (% REL) Fluid: SGF @ 100 rpm Interval - 30 min | 97.0 | 98.4 | 91.4 | NLT 80% @ 30 min |
| Storage Conditions | | | | RT = Room Temperature 15–30° C. 37/75 = 35–40° C. with 70–80% Relative Humidity N/A color = White or no ref. |

| Parameter & Method | Initial | 1M 37/75 | 2M 37/75 | 3M 37/75 | 6M 37/75 | Specifications |
|---|---|---|---|---|---|---|
| Potency (mg/g) | 671.5 | 676.7 | 688.9 | 644.4 | 626.1 | 629.0–839.0 mg/g |
| Potency (% of Theory) | 95.7 | 96.4 | 98.1 | 91.8 | 89.2 | |
| Potency (% of Initial) | 100.0 | 100.8 | 102.6 | 96.0 | 93.2 | 90.0–120.0% LC |
| Loss of Dryness (% w/w) | 0.60 | 1.09 | 1.38 | 1.60 | 1.84 | Report Value |
| Water (%) | 12.55 | 12.16 | 11.85 | 12.72 | 11.58 | Report Value |
| Appearance Pass | Pass | Pass | Pass | Pass | Pass | White to Off White Free Flowing, Uniform Spheres |
| Color | N/A | N/A | 461C | 393U | 393U | Report Value |
| Odor | Pass | Pass | Pass | Pass | Pass | Compares to Standard |
| Taste Pass | Pass | Pass | Pass | Pass | Pass | None to Slight Bitter |
| Bulk Density (g/ml) | 0.488 | 0.465 | 0.496 | 0.471 | 0.496 | Report Value |
| Dissolution, (% REL) Fluid: SGF @ 100 rpm Interval - 30 min | 97.0 | 101.9 | 93.7 | 100.4 | 80.2 | NLT 80% @ 30 min |
| Storage Conditions | | | | | | RT = Room Temperature 15–30° C. 37/75 = 35–40° C. with 70–80% Relative Humidity N/A color = White or no ref. |

TABLE 6B

STORAGE CONDITIONS

Lot #: 870630A-1  Theoretical Potency (mg/g): 697.2

| Parameter & Method | Initial | 3M RT | 6M RT | 9M RT | Specifications |
|---|---|---|---|---|---|
| Potency (mg/g) | 697.9 | 707.3 | 683.5 | 692.9 | 629.0–839.0 mg/g |
| Potency (% of Theory) | 100.10 | 101.45 | 98.03 | 99.38 | |
| Potency (% of Initial) | 100.00 | 101.35 | 97.94 | 99.28 | 90.0–120.0% LC |
| Loss of Dryness (% w/w) | 1.05 | 0.77 | 1.19 | 1.25 | Report Value |
| Water (%) | 13.46 | 11.94 | 11.20 | 9.72 | Report Value |
| Appearance | Pass | Pass | Pass | Pass | White to Off White Free Flowing, Uniform Spheres |
| Color | N/A | N/A | N/A | N/A | Report Value |
| Odor | Pass | Pass | Pass | Pass | Compares to Standard |
| Taste | Pass | Pass | Pass | Pass | None to Slight Bitter |
| Bulk Density (g/ml) | 0.533 | 0.516 | 0.503 | 0.481 | Report Value |
| Dissolution (% REL) Fluid: SGF @ 100 rpm Interval - 30 min | 99.4 | 102.1 | 101.9 | 92.2 | NLT 80% @ 30 min |
| Storage Conditions | | | | | RT = Room Temperature 15–30° C. 37/75 = 35–40° C. with 70–80% Relative Humidity N/A color = white or no ref. |

| Parameter & Method | Initial | 1M 37/75 | 3M 37/75 | 6M 37/75 | Specifications |
|---|---|---|---|---|---|
| Potency (mg/g) | 697.9 | 680.5 | 684.8 | 620.5 | 629.0–839.0 mg/g |
| Potency (% of Theory) | 100.10 | 97.60 | 98.22 | 89.00 | |
| Potency (% of Initial) | 100.0 | 97.51 | 98.12 | 88.91 | 90.0–120.0% LC |
| Loss of Dryness (% w/w) | 1.05 | 1.49 | 1.08 | 2.40 | Report Value |
| Water (%) | 13.46 | 12.01 | 12.07 | 11.60 | Report Value |
| Appearance | Pass | Pass | Pass | Pass | White to Off White Free Flowing, Uniform Spheres |
| Color | N/A | #461C | #393U | #101C | Report Value |
| Odor | Pass | Pass | Pass | Pass | Compares to Standard |
| Taste | Pass | Pass | Pass | Pass | None to Slight Bitter |

TABLE 6B-continued

| Lot #: 870630A-1 | STORAGE CONDITIONS | | | | |
|---|---|---|---|---|---|
| | Theoretical Potency (mg/g): 697.2 | | | | |
| Bulk Density (g/ml) | 0.533 | 0.496 | 0.497 | 0.508 | Report Value |
| Dissolution (% REL) | | | | | |
| Fluid: SGF @ 100 rpm | | | | | |
| Interval - 30 min | 99.4 | 91.7 | 105.2 | 86.4 | NLT 80% @ 30 min |
| Storage Conditions | RT = Room Temperature 15-30° C. | | | | |
| | 37/75 = 35-40° C. with 70-80% Relative Humidity | | | | |
| | N/A odor = white or no ref. | | | | |

TABLE 6C

| Lot #: 870915B-2 | STORAGE CONDITIONS | | | |
|---|---|---|---|---|
| | Theoretical Potency (mg/g): 701.0 | | | |
| Parameter & Method | Initial | 3M RT | 6M RT | Specifications |
| Potency (mg/g) | 696.4 | 664.9 | 683.3 | 629.0-839.0 mg/g |
| Potency (% of Theory) | 99.3 | 94.9 | 97.5 | |
| Potency (% of Initial) | 100.0 | 95.5 | 98.1 | 90.0-120.0% LC |
| Loss of Dryness (% w/w) | 1.06 | 0.61 | 0.80 | Report Value |
| Water (%) | 12.99 | 12.19 | 11.69 | Report Value |
| Appearance | Pass | Pass | Pass | White to Off White Free Flowing, Uniform Spheres |
| Color | N/A | N/A | N/A | Report Value |
| Odor | Pass | Pass | Pass | Compares to Standard |
| Taste | Pass | Pass | Pass | None to Slight Bitter |
| Bulk Density (g/ml) | 0.501 | 0.496 | 0.513 | Report Value |
| Dissolution (% REL) | | | | |
| Fluid: SGF @ 100 rpm | | | | |
| Interval - 30 min | 97.1 | 101.3 | 93.9 | NLT 80% @ 30 min |
| Storage Conditions | RT = Room Temperature 15-30° C. | | | |
| | 37/75 = 35-40° C. with 70-80% Relative Humidity | | | |
| | N/A color = White or no ref. | | | |

| Parameter & Method | Initial | 1M 37/75 | 2M 37/75 | 3M 37/75 | 6M 37/75 | Specifications |
|---|---|---|---|---|---|---|
| Potency (mg/g) | 696.4 | 681.4 | 675.2 | 667.0 | 617.1 | 629.0-839.0 mg/g |
| Potency (% of Theory) | 99.3 | 97.2 | 96.3 | 95.1 | 88.0 | |
| Potency (% of Initial) | 100.0 | 97.8 | 97.0 | 95.8 | 88.6 | 90.0-120.0% LC |
| Loss of Dryness (% w/w) | 1.06 | 1.05 | 1.24 | 1.41 | 2.05 | Report Value |
| Water (%) | 12.99 | 12.46 | 13.26 | 12.56 | 11.95 | Report Value |
| Appearance | Pass | Pass | Pass | Pass | Pass | White to Off White Free Flowing, Uniform Spheres |
| Color | N/A | N/A | 461C | 393U | 393U | Report Value |
| Odor | Pass | Pass | Pass | Pass | Pass | Compares to Standard |
| Taste | Pass | Pass | Pass | Pass | Pass | None to Slight Bitter |
| Bulk Density (g/ml) | 0.501 | 0.466 | 0.495 | 0.489 | 0.497 | Report Value |
| Dissolution, (% REL) | | | | | | |
| Fluid: SGF @ 100 rpm | | | | | | |
| Interval - 30 min | 97.1 | 102.4 | 100.2 | 103.1 | 82.5 | NLT 80% @ 30 min |
| Storage Conditions | RT = Room Temperature 15-30° C. | | | | | |
| | 37/75 = 35-40° C. with 70-80% Relative Humidity | | | | | |
| | N/A color = White or no ref. | | | | | |

TABLE 6D

| Lot #: 870923B-1 | STORAGE CONDITIONS | | | |
|---|---|---|---|---|
| | Theoretical Potency (mg/g): 702.0 | | | |
| Parameter & Method | Initial | 3M RT | 6M RT | Specifications |
| Potency (mg/g) | 677.6 | 656.7 | 683.7 | 629.0-839.0 mg/g |
| Potency (% of Theory) | 96.5 | 93.5 | 97.4 | |
| Potency (% of Initial) | 100.0 | 96.9 | 100.9 | 90.0-120.0% LC |
| Loss of Dryness (% w/w) | 0.89 | 0.51 | 0.66 | Report Value |
| Water (%) | 12.59 | 12.05 | 12.04 | Report Value |
| Appearance | Pass | Pass | Pass | White to Off White Free Flowing, Uniform Spheres |
| Color | N/A | N/A | N/A | Report Value |
| Odor | Pass | Pass | Pass | Compares to Standard |
| Taste | Pass | Pass | Pass | None to Slight Bitter |
| Bulk Density (g/ml) | 0.507 | 0.480 | 0.506 | Report Value |
| Dissolution (% REL) | | | | |
| Fluid: SGF @ 100 rpm | | | | |
| Interval - 30 min | 98.1 | 101.4 | 95.6 | NLT 80% @ 30 min |
| Storage Conditions | RT = Room Temperature 15-30° C. | | | |

TABLE 6D-continued

STORAGE CONDITIONS

Lot #: 870923B-1   Theoretical Potency (mg/g): 702.0

37/75 = 35–40° C. with 70–80% Relative Humidity
N/A color = White or no ref.

| Parameter & Method | Initial | 1M 37/75 | 2M 37/75 | 3M 37/75 | 6M 37/75 | Specifications |
|---|---|---|---|---|---|---|
| Potency (mg/g) | 677.6 | 657.3 | 679.2 | 682.0 | 618.7 | 629.0–839.0 mg/g |
| Potency (% of Theory) | 96.5 | 93.6 | 96.8 | 97.2 | 88.1 | |
| Potency (% of Initial) | 100.0 | 97.0 | 100.2 | 100.6 | 91.3 | 90.0–120.0% LC |
| Loss of Dryness (% w/w) | 0.89 | 0.95 | 1.27 | 1.31 | 2.05 | Report Value |
| Water (%) | 12.59 | 12.18 | 13.65 | 12.19 | 11.05 | Report Value |
| Appearance | Pass | Pass | Pass | Pass | Pass | White to Off White Free Flowing, Uniform Spheres |
| Color | N/A | N/A | 400C | 393U | 393U | Report Value |
| Odor | Pass | Pass | Pass | Pass | Pass | Compares to Standard |
| Taste | Pass | Pass | Pass | Pass | Pass | None to Slight Bitter |
| Bulk Density (g/ml) | 0.507 | 0.471 | 0.495 | 0.486 | 0.500 | Report Value |
| Dissolution, (% REL) Fluid: SGF @ 100 rpm | | | | | | |
| Interval - 30 min | 98.1 | 103.1 | 101.2 | 103.5 | 83.1 | NLT 80% @ 30 min |

Storage Conditions   RT = Room Temperature 15–30° C.
37/75 = 35–40° C. with 70–80% Relative Humidity
N/A color = White or no ref.

TABLE 6E

STORAGE CONDITIONS

Lot #: 870923C-1   Theoretical Potency (mg/g): 702.0

| Parameter & Method | Initial | 3M RT | 6M RT | Specifications |
|---|---|---|---|---|
| Potency (mg/g) | 671.5 | 692.2 | 687.4 | 629.0–839.0 mg/g |
| Potency (% of Theory) | 95.7 | 98.6 | 97.9 | |
| Potency (% of Initial) | 100.0 | 103.1 | 102.4 | 90.0–120.0% LC |
| Loss of Dryness (% w/w) | 0.60 | 0.59 | 0.52 | Report Value |
| Water (%) | 12.55 | 12.10 | 11.58 | Report Value |
| Appearance | Pass | Pass | Pass | White to Off White Free Flowing, Uniform Spheres |
| Color | N/A | N/A | N/A | Report Value |
| Odor | Pass | Pass | Pass | Compares to Standard |
| Taste | Pass | Pass | Pass | None to Slight Bitter |
| Bulk Density (g/ml) | 0.488 | 0.495 | 0.509 | Report Value |
| Dissolution (% REL) Fluid: SGF @ 100 rpm | | | | |
| Interval - 30 min | 97.0 | 100.0 | 91.7 | NLT 80% @ 30 min |

Storage Conditions   RT = Room Temperature 15–30° C.
37/75 = 35–40° C. with 70–80% Relative Humidity
N/A color = White or no ref.

| Parameter & Method | Initial | 1M 37/75 | 2M 37/75 | 3M 37/75 | 6M 37/75 | Specifications |
|---|---|---|---|---|---|---|
| Potency (mg/g) | 671.5 | 671.8 | 648.9 | 689.2 | 622.8 | 629.0–839.0 mg/g |
| Potency (% of Theory) | 95.7 | 95.7 | 92.4 | 98.2 | 88.7 | |
| Potency (% of Initial) | 100.0 | 100.0 | 96.6 | 102.6 | 92.7 | 90.0–120.0% LC |
| Loss of Dryness (% w/w) | 0.60 | 1.01 | 1.39 | 1.35 | 1.83 | Report Value |
| Water (%) | 12.55 | 10.93 | 12.94 | 11.67 | 11.50 | Report Value |
| Appearance | Pass | Pass | Pass | Pass | Pass | White to Off White Free Flowing, Uniform Spheres |
| Color | N/A | N/A | 461C | 393U | 393U | Report Value |
| Odor | Pass | Pass | Pass | Pass | Pass | Compares to Standard |
| Taste | Pass | Pass | Pass | Pass | Pass | None to Slight Bitter |
| Bulk Density (g/ml) | 0.488 | 0.470 | 0.495 | 0.480 | 0.501 | Report Value |
| Dissolution, (% REL) Fluid: SGF @ 100 rpm | | | | | | |
| Interval - 30 min | 97.0 | 101.7 | 93.4 | 102.7 | 81.6 | NLT 80% @ 30 min |

Storage Conditions   RT = Room Temperature 15–30° C.
37/75 = 35–40° C. with 70–80% Relative Humidity
N/A color = White or no ref.

While the invention has been disclosed by reference to the details of various embodiments of the invention, it is understood that this disclosure is intended in an illustrative rather than in a limiting sense, as it is contemplated that modifications will occur to those skilled in the art, within the spirit of the invention and the scope of the appended claims.

What is claimed is:

1. A microencapsulated granule comprising a mixture of amoxicillin and a binder as an active coating in a ratio of about 5:1 to about 13:1 on a seed, said granule having an activity density greater than about 0.200 g/ml and a diameter less than 1000 microns, and said binder selected from the group consisting of hydroxypropyl methylcellulose phthalate, hydroxypropyl methylcellulose, polyvinyl pyrrolidone, polyethylene glycol, poleyethylene oxide, hydroxypropyl cellulose, cellulose acetate phthalate, polyvinyl acetate phthalate and combinations thereof.

2. A dosage delivery system comprising a plurality of amoxicillin microencapsulated granules as described in claim 1, contained in a unit dose delivery system.

3. The microencapsulated granule of claim 1 wherein the active coating is applied to the seed as an active coating composition comprising about 29% by weight to about 33% by weight amoxicillin, about 2% by weight to about 6% by weight binder and a solvent.

4. The microencapsulated granule of claim 3 wherein the binder comprises hydroxypropyl methylcellulose 5. The microencapsulated granule of claim 3 wherein the solvent may be selected from the group consisting of water, ethanol, methanol, isopropanol, acetone, methylene chloride, chloroform, ethyl acetate, carbon tetrachloride, benzene, methyl ethyl ketone and combinations thereof.

6. The microencapsulated granule of claim 1 further comprising a mixture of about 35% by weight to about 55% by weight ethylcellulose and about 45% by weight to about 65% by weight polyethylene glycol as a taste mask coating over the active coating.

7. The microencapsulated granule of claim 6 wherein the polyethylene glycol has a molecular weight between about 1000 and about 9000.

8. The microencapsulated granule of claim 7 wherein the polyethylene glycol has an average molecular weight of about 8000.

9. The microencapsulated granule of claim 8 wherein the ethylcellulose is a standard-type ethylcellulose with a Ubbelohde viscosity of about 10 cps for a 5% by weight solution at about 25° C.

10. The microencapsulated granule of claim 9 wherein the mixture comprises about 45% by weight ethylcellulose and about 55% by weight polyethylene glycol.

11. The microencapsulated granule of claim 6 wherein the taste mask coating is applied as a taste mask coating composition comprising a solution of about 5% by weight of the ethylcellulose/polyethylene glycol mixture in a solvent.

12. The microencapsulated granule of claim 11 wherein the solvent may be selected from the group consisting of ethyl acetate, ethylene dichloride, benzene, toluene, xylene, butyl acetate, acetone, methanol, ethanol, butanol, carbon tetrachloride, water and combinations thereof.

13. The microencapsulated granule of claim 12 wherein the solvent comprises about 75% by weight to about 95% by weight acetone and about 5% by weight to about 25% by weight water.

14. The microencapsulated granule of claim 6 further comprising a sufficient amount of an antistatic agent to coat the granule, said antistatic agent selected from the group consisting of silicon dioxide, talc, magnesium stearate, calcium stearate, polacrilin, stearic acid and combinations thereof.

15. The microencapsulated granule of claim 14 wherein the antistatic agent comprises about 0.75% by weight silicon dioxide.

16. A process for manufacturing an amoxicillin microencapsulated granule having a ratio of amoxicillin to a binder of about 5:1 to about 13:1, an activity density greater than about 0.200 g/ml and a diameter less than about 1000 microns, comprising applying an active coating composition to an inert seed to form an active seed, said active coating composition comprising about 29% by weight to about 33% by weight amoxicillin, about 2% by weight to about 6% by weight binder and a solvent.

17. A process for manufacturing an amoxicillin microencapsulated granule having a ratio of amoxicillin to a binder of about 5:1 to about 13:1, an activity density greater than about 0.200 g/ml and a diameter less than about 1000 microns, comprising applying an active coating composition to an active drug crystal to form an active seed, said active coating composition comprising about 29% by weight to about 33% by weight amoxicillin, about 2% by weight to about 6% by weight binder and a solvent.

18. The process of claim 16 wherein:
the binder may be selected from the group consisting of hydroxypropyl methylcellulose phthalate, hydroxypropyl methylcellulose, polyvinyl pyrrolidone, polyethylene glycol, polyethylene oxide, hydroxypropyl cellulose, cellose acetate phthalate, polyvinyl acetate phthalate and combinations thereof; and
the solvent may be selected from the group consisting of water, ethanol, methanol, isopropanol, acetone, methylene chloride, chloroform, ethyl acetate, carbon tetrachloride, benzene, methyl ethyl ketone and combinations thereof.

19. The process of claim 16 further comprising the application of a taste mask coating composition to the active seed.

20. The process of claim 19 wherein the taste mask coating composition comprises a dispersion of about 5% by weight of a mixture of ethylcellulose and polyethylene glycol in a solvent.

21. The process of claim 20 wherein the mixture comprises about 35% by weight to about 55% by weight ethylcellulose and about 45% by weight to about 65% by weight polyethylene glycol, and the solvent may be selected from the group consisting of ethyl acetate, ethylene dichloride, benzene, toluene, xylene, butyl acetate, acetone, methanol, ethanol, butanol, carbon tetrachloride, water and combinations thereof.

22. The process of claim 21 wherein the polyethylene glycol has a molecular weight between about 1000 and about 9000.

23. The process of claim 22 wherein the polyethylene glycol has an average molecular weight of about 8000.

24. The process of claim 23 wherein the ethylcellulose is a standard type ethylcellulose with a Ubbelohde viscosity of about 10 cps for a 5% by weight solution at about 25° C.

25. The process of claim 24 wherein the mixture comprises about 45% by weight ethylcellulose and about 55% by weight polyethylene glycol and the solvent comprises about 75% by weight to about 95% by weight acetone and about 5% by weight to about 25% by weight water.

26. The process of claim 25 wherein the mixture of ethylcellulose and polyethylene glycol is about 5% by weight of the solution.

27. The process of claim 19 further comprising applying a sufficient amount of an antistatic agent to coat the microgranules.

28. The process of claim 27 wherein the antistatic agent may be selected from the group consisting of silicon dioxide, talc, magnesium stearate, calcium stearate, polacrilin, stearic acid and combinations thereof.

29. The process of claim 27 wherein the active coating composition, the taste mask coating composition and the antistatic agent are applied using a fluidized bed technique.

30. A dosage delivery system comprising a plurality of amoxicillin microencapsulated granules as described in claim 1, in a tablet form.

31. A dosage delivery system comprising a plurality of amoxicillin microencapsulated granules as described in claim 1, contained in a water soluble capsule.

32. A dosage delivery system comprising a plurality of amoxicillin microencapsulated granules as described in claim 1, contained in a flowable material dispenser.

* * * * *